United States Patent
Sharma et al.

(10) Patent No.: US 6,881,852 B2
(45) Date of Patent: Apr. 19, 2005

(54) PROCESS OF PURIFICATION OF PACLITAXEL AND DOCETAXEL

(75) Inventors: Arun Prakash Sharma, Nadia (IN); Jyan Shankar Mahanty, Nadia (IN); Subrata Sarkar, Nadia (IN)

(73) Assignee: Dabur India Limited, Nadia (IN)

( * ) Notice: Subject to any disclaimer, the term of this patent is extended or adjusted under 35 U.S.C. 154(b) by 0 days.

(21) Appl. No.: 10/358,384

(22) Filed: Feb. 5, 2003

(65) Prior Publication Data

US 2003/0225291 A1 Dec. 4, 2003

Related U.S. Application Data

(60) Provisional application No. 60/353,995, filed on Feb. 5, 2002.

(51) Int. Cl.$^7$ ............................................. C07D 305/14
(52) U.S. Cl. ...................................... 549/510; 549/511
(58) Field of Search ................................. 549/510, 511

(56) References Cited

U.S. PATENT DOCUMENTS

| | | | |
|---|---|---|---|
| 5,476,954 A | 12/1995 | Bourzat et al. | |
| 5,616,739 A | 4/1997 | Mas et al. | |
| 5,637,723 A | 6/1997 | Commercon et al. | |
| 6,002,022 A | 12/1999 | Authelin et al. | |
| 6,022,985 A | 2/2000 | Authelin et al. | |
| 6,197,980 B1 | 3/2001 | Durand et al. | |
| 6,506,905 B1 | 1/2003 | Prakash et al. | |

OTHER PUBLICATIONS

U.S. patent application Ser. No. 10/430,433, Sharma et al., filed May 7, 2003.

U.S. patent application Ser. No. 10/358,384, Sharma et al., filed Feb. 5, 2003.

U.S. patent application Ser. No. 10/419,782, Sharma et al., filed Apr. 22, 2003.

U.S. patent application Ser. No. 10/213,431, Sharma et al., filed Aug. 7, 2002.

Wani et al., J. Am. Chem. Soc., vol. 93, pp. 2325–2326 (1971).

United States Pharmacopoeia, USP 27, pp. 1394–1397 (2004).

U.S. Appl. No. 10/431,499, filed Aug. 5, 2003, Sharma et al.

*Primary Examiner*—Ba K. Trinh
(74) *Attorney, Agent, or Firm*—Marina V. Schneller; Venable LLP

(57) ABSTRACT

A process for the purification of paclitaxel or docetaxel comprising: (a) mixing crude paclitaxel with a mixture of solvents such as alkane and chlorinated alkane, filtering the solid followed by drying to obtain paclitaxel or docetaxel of increased purity; (b) repeating step (a) one or more times to obtain paclitaxel or docetaxel of increased purity; (c) dissolving the solid obtained from step (b) in alkyl ketone followed by adding alkane thereto, filtering and drying the solid thus formed to obtain paclitaxel or docetaxel of increased purity; (d) repeating step (c) one or more times to increase the purity of paclitaxel or docetaxel; (e) dissolving the paclitaxel or docetaxel obtained from step (d) in alkanol and then adding water, filtering and drying the solid thus formed, to obtain paclitaxel of increased purity; (f) dissolving the solid obtained from step (e) in alkyl ketone, filtering, followed by adding alkane to the filtrate, filtering and drying the solid thus formed to obtain pure paclitaxel or pure docetaxel.

28 Claims, No Drawings

PROCESS OF PURIFICATION OF PACLITAXEL AND DOCETAXEL

This application claims the benefit of Provisional application Ser. No. 60/353,995, filed Feb. 5, 2002.

FIELD OF INVENTION

The present invention relates to the process of purification of Paclitaxel and Docetaxel.

BACKGROUND OF THE INVENTION

Paclitaxel is a well-known and approved (FDA AND HPB) chemotherapeutic drug for treatment of metastatic cancer. It is a natural product, isolated from a number of Taxus species.

However, the concentration of Paclitaxel in its natural resources is very low, in the order of 0.004 to 0.01% (w/w). Also, several structurally similar compounds occur along with Paclitaxel in Taxus species. This makes extraction and purification of the compound almost impractical in commercial scale.

Semisyntheses of paclitaxel from 10-DAB address the problem of its availability. However, purification of the synthetic compound to pharmaceutical grade remains challenging due to formation of a number of degradation products during synthesis. Similar problems are encountered in purification of Docetaxel, a synthetic analog of Paclitaxel.

Classical low pressure column chromatography for the purification of Paclitaxel and Docetaxel involves use of silica gel or alumina which are strong absorbent and may adversely participate in the separation process resulting in low selectivity and recovery. Also, handling and destruction of silica or alumina contaminated with toxic material is problematic.

Reverse phase chromatography on bonded silica gel column can be conducted only on a small laboratory scale. Furthermore, the process is labor and capital intensive.

OBJECTS OF THE INVENTION

An object of this invention is to provide a process for obtaining pharmaceutical grade paclitaxel and docetaxel from natural crude paclitaxel or synthetic crude paclitaxel or docetaxel.

Another object of this invention is to provide a simple and cost effective method for isolation of pharmaceutical grade pure paclitaxel/docetaxel from synthetic crude paclitaxel/docetaxel and natural crude paclitaxel.

Still another object of this invention is to propose a solvent-based purification method, which can be scaled up easily.

Further, object of the invention is to propose a process for purification, which does not require any sophisticated instruments.

SUMMARY OF THE INVENTION

According to this invention there is provided a process of purification of Paclitaxel and Docetaxel comprising:
a) treating taxene (e.g. paclitaxel, docetaxel of 40–55% w/w purity and 60–70% w/w chromatographic purity) with a mixture of alkane and chlorinated alkane to obtain a crude product of 65–75% w/w purity;
b) dissolving the above solid in alkyl ketone followed by slow addition of alkane to increase the purity to 85–95% w/w;
c) dissolving the solid obtained in step b in alkanol and then precipitating by water to obtain a purity of 97–98% w/w;
d) dissolving taxane obtained from step c in alkyl ketone. Subsequent slow addition of alkane results in the precipitation of pure paclitaxel/docetaxel. The latter is filtered and dried to obtain purity of 98–102%

Repetition of one or more steps could be required to achieve the above mentioned results.

DETAILED DESCRIPTION OF THE PREFERRED EMBODIMENT

The present invention provides a simple and economic procedure for purification of Paclitaxel and Docetaxel. It does not require any sophisticated instrument and can be scaled up easily.

EXAMPLE

Step 1

Crude taxane (C. P. 60–70%; assay 40–55%) is added to mixture of chlorinated alkane and alkane (1:9; 10 times). The mixture is stirred for 4 h and then filtered under vacuum to obtain a purity of 55–65% w/w. Step 1 is repeated to increase the purity of the crude product to 65–75% w/w. The preferred chlorinated alkane is dichloromethane and the preferred alkane is hexane.

Step 2

The crude obtained from step 1 is dissolved in alkyl ketone (6 times of crude weight) preferably acetone at 20–45° C. The solution is cooled and then alkane (18 times of crude) preferably hexane is added under stirring. The mixture is further stirred for 4 h and then filtered. The solid obtained is dried under vacuum. Step 2 is repeated to obtain an assay of 85–90%. Incase of Docetaxel the target purity is 90–95% at this stage.

Step 3

The solid obtained from step 2 is dissolved in alkanol, preferably methanol (30 times of crude weight) at 20–40° C. The solution is cooled and then an equal amount of distilled water is added under stirring. The mixture is cooled and then further stirred for 4 h. The slurry thus obtained is filtered and the residue is dissolved in chloroalkane, preferably dichloromethane. After layer separation to discard the aqueous layer, the organic layer is evaporated to obtain taxane of purity 97–9% (w/w).

Step 4

The taxane obtained from step 3 is dissolved in 15–20 times alkyl ketone, preferably acetone at room temperature. The solution is filtered through 10-micron filter paper. To the filtered solution alkane, preferably hexane (2–2.3 times with respect to alkyl ketone) is added slowly. The mixture is stirred further for 2–4 h and then filtered. The solid, thus obtained, is dried under vacuum to obtain paclitaxel/docetaxel of purity 98–102%.

The present invention will now be illustrated in more detail by the way of examples.

EXAMPLES

Purification of Paclitaxel

STEP-1 (Alkane:chlorinated Alkane Purification)

To a mixture of dichloromethane-hexane (1:9, 15 L) crude paclitaxel 1.5 Kg (52% w/w purity and 66.5% chromatographic purity) is added under stirring. Stirring is continued for 4–6 h at 20–25° C. The solid thus obtained is filtered and then dried under reduced pressure at 50° C. for 6 h.

Yield: 980 gm (w/w purity 75.0%). The basis w/w refers, here and in the description below, to a quantitative assay of the compound which is calculated against a reference standard weight/weight. Below the acronym NMT indicates 'not more than'.

STEP-2 (Alkane:alkyl Ketone Purification)

Paclitaxel (980 gm, obtained from step-1) is added to acetone (6.0 L). The mixture is stirred at 30° C. to get a clear solution. Hexane (18 L) is added slowly under stirring. A white precipitate appears. Stirring is continued at for additional 4 h. The material is filtered and then dried under reduced pressure at 60° C. for 6 h.

Yield: 790 gm (w/w purity 90.8%).

STEP-3 (Alkanol:water Purification)

Paclitaxel (790 gm, obtained from step-2) is added to methanol (23.5 L). The mixture is stirred at 30° C. to get a clear solution. Water (23.5 L) is then added slowly under stirring. A white precipitate appears. Stirring is continued at for additional 4 h. The material is filtered and the wet cake is dissolved in dichloromethane (8.0 L). The water layer is separated from organic layer. The organic layer is evaporated and dried under reduced pressure. at 60° C. for 3 h under reduced pressure.

Yield: 720 gm (w/w purity 98.2%).

STEP-4 (Alkane:alkyl Ketone Purification)

Paclitaxel (720 gm, obtained from step-3) is added to acetone (14.4 L). The mixture is stirred at 30° C. to get clear solution and then filtered it through 10 micron filter paper. Hexane (33 L) is added slowly under stirring. A white precipitate appears. Stirring is continued at for additional 4 h. The material is filtered and then dried under reduced pressure at 60° C. for 6 h.

Yield 650 gm (w/w purity 99.5%, chromatographic purity 99.6% and total impurity NMT 0.4%).

Purification of Docetaxel

STEP-1 (Alkane:chlorinated Alkane Purification)

To a mixture of dichloromethane-hexane (15:85, 15 L) crude docetaxel (1.5 Kg, 53% w/w purity and 70% chromatographic purity) is added under stirring. Stirring is continued for 4 h at 20–25° C. The solid is filtered and then dried under reduced pressure at 50° C. for 6 h.

Yield: 1005 gm (w/w purity 73.0%).

STEP-2 (Alkane:alkyl Ketone Purification)

Docetaxel (1005 gm, obtained from step-1) is added to acetone (10.0 L). The mixture is stirred at 30° C. to get a clear solution. Hexane (23 L) is then added slowly under stirring. A white precipitate appears. Stirring is continued at for additional 2 h. The material is filtered and then dried under reduced pressure at 60° C. for 6 h.

Yield: 725 gm (w/w purity 95.8%).

STEP-3 (Alkanol:water Purification)

Docetaxel (725 gm, obtained from step-2) is added to methanol (21.7 L). The mixture is stirred at 30° C. to get a clear solution and then water (21.7 L) is added slowly under stirring. A white precipitate appears. Stirring is continued at for additional 2 h. The material is filtered and dried under vacuum at 60° C. for 6 h. Yield: 680 gm (w/w purity 97.2%).

STEP-4 (Alkane:alkyl Ketone Purification)

Docetaxel (680 gm, obtained from step-3) is added to acetone (13.6 L). The mixture is stirred at 30° C. to get clear solution and then filtered it through 10 micron filter. Hexane (27.2 L) is added slowly under stirring. A white precipitate appears. Stirring is continued at for additional 4 h. The material is filtered and then dried under reduced pressure at 60° C. for 6 h.

Yield 630 gm (w/w purity 99.3%, chromatographic purity 99.65% and total impurity NMT 0.35%).

We claim:

1. A process for the purification of paclitaxel comprising:
   a) mixing crude paclitaxel with a mixture of solvents selected from the group consisting of alkane and chlorinated alkane, filtering the solid followed by drying to obtain paclitaxel of increased purity;
   b) repeating step (a) one or more times to obtain paclitaxel of increased purity;
   c) dissolving the solid obtained from step (b) in alkyl ketone followed by adding alkane thereto, filtering and drying the solid thus formed to obtain paclitaxel of increased purity;
   d) repeating step (c) one or more times to increase the purity of paclitaxel;
   e) dissolving the paclitaxel obtained from step (d) in alkanol and then adding water, filtering and drying the solid thus formed, to obtain paclitaxel of increased purity;
   f) dissolving the solid obtained from step (e) in alkyl ketone, filtering, followed by adding alkane to the filtrate, filtering and drying the solid thus formed to obtain pure paclitaxel.

2. The process as claimed in claim 1, wherein the mother liquor obtained in step (c) and (f) are concentrated to remove solvents to obtain crude paclitaxel which subsequently can be purified by following the above mentioned steps.

3. The process as claimed in claim 1, wherein the alkane solvents used are preferably selected from hexane and pentane.

4. The process as claimed in claim 1, wherein the chlorinated alkane is preferably selected from dichloromethane, chloroform.

5. The process as claimed in claim 1, wherein the alkyl ketone is preferably selected from acetone, ethyl methyl ketone.

6. The process as claimed in claim 1, wherein the alkanol is preferably selected from methanol, ethanol.

7. The process as claimed in claim 1, wherein said crude paclitaxel is of 40–55% w/w purity and 60–70% chromatographic purity.

8. The process as claimed in claim 1, wherein the crude paclitaxel is obtained from semi synthetic or natural sources.

9. The process as claimed in claim 1, wherein the purity of paclitaxel after step-(a) is 60–70% w/w.

10. The process as claimed in claim 1, wherein the purity of paclitaxel after step-(b) is 65–75% w/w.

11. The process as claimed in claim 1, wherein the purity of paclitaxel after step-(c) is 80–85% w/w.

12. The process as claimed in claim 1, wherein the purity of paclitaxel after step-(d) is 85–90% w/w.

13. The process as claimed in claim 1, wherein the purity of paclitaxel after step-(e) is 97–98% w/w.

14. The process as claimed in claim 1, wherein the purity of paclitaxel after step-(f) is 98–102% w/w.

15. A process for the purification of docetaxel comprising:
   a) mixing crude docetaxel with a mixture of solvents selected from the group consisting of alkane and chlorinated alkane, filtering the solid followed by drying to obtain paclitaxel of increased purity;
   b) repeating step (a) one or more times to obtain docetaxel of increased purity;
   c) dissolving the solid obtained from step (b) in alkyl ketone followed by adding alkane thereto, filtering and drying the solid thus formed to obtain docetaxel of increased purity;
   d) repeating step (c) one or more times to increase the purity of paclitaxel;
   e) dissolving the docetaxel obtained from step (d) in alkanol and then adding water, filtering and drying the solid thus formed, to obtain docetaxel 1 of increased purity;

f) dissolving the solid obtained from step (e) in alkyl ketone, filtering, followed by adding alkane to the filtrate, filtering and drying the solid thus formed to obtain pure docetaxel.

16. The process as claimed in claim 15, wherein the mother liquor obtained in step (c) and (f) are concentrated to remove solvents to obtain crude docetaxel which subsequently can be purified by following the above mentioned steps.

17. The process as claimed in claim 15, wherein the alkane solvents used are preferably selected from hexane and pentane.

18. The process as claimed in claim 15, wherein the chlorinated alkane is preferably selected from dichloromethane, chloroform.

19. The process as claimed in claim 15, wherein the alkyl ketone is preferably selected from acetone, ethyl methyl ketone.

20. The process as claimed in claim 15, wherein the alkanol is preferably selected from methanol, ethanol.

21. The process as claimed in claim 15, wherein said crude docetaxel is of 40–55% w/w purity and 60–70% chromatographic purity.

22. The process as claimed in claim 15, wherein the crude docetaxel is obtained from semi synthetic route.

23. The process as claimed in claim 15, wherein the purity of docetaxel after step-(a) is 60–70% w/w .

24. The process as claimed in claim 15, wherein the purity of docetaxel after step-(b) is 65–75% w/w.

25. The process as claimed in claim 15, wherein the purity of docetaxel after step-(c) is 85–90% w/w.

26. The process as claimed in claim 15, wherein the purity of docetaxel after step-(d) is 90–95% w/w.

27. The process as claimed in claim 15, wherein the purity of docetaxel after step-(e) is 97–98% w/w.

28. The process as claimed in claim 15, wherein the purity of docetaxel after step-(f) is 98–102% w/w.

* * * * *